United States Patent
Sakurai (10) Patent No.: US 11,912,188 B2
(45) Date of Patent: Feb. 27, 2024

(54) ENTRANCE HANDRAIL

(71) Applicant: TOYOTA JIDOSHA KABUSHIKI KAISHA, Aichi-ken (JP)

(72) Inventor: Hideyuki Sakurai, Toyota (JP)

(73) Assignee: TOYOTA JIDOSHA KABUSHIKI KAISHA, Aichi-Ken (JP)

( * ) Notice: Subject to any disclaimer, the term of this patent is extended or adjusted under 35 U.S.C. 154(b) by 379 days.

(21) Appl. No.: 17/399,051

(22) Filed: Aug. 11, 2021

(65) Prior Publication Data
US 2022/0063472 A1   Mar. 3, 2022

(30) Foreign Application Priority Data

Aug. 27, 2020 (JP) ................................ 2020-143772

(51) Int. Cl.
*B60N 3/02* (2006.01)
*A61L 2/10* (2006.01)

(52) U.S. Cl.
CPC ............... *B60N 3/023* (2013.01); *A61L 2/10* (2013.01); *A61L 2202/16* (2013.01)

(58) Field of Classification Search
CPC ......... B60N 3/02; B60N 3/023; E05B 1/0069; A61L 2202/16
USPC ....................................................... 296/1.02
See application file for complete search history.

(56) References Cited

U.S. PATENT DOCUMENTS

| | | | | |
|---|---|---|---|---|
| 7,716,789 B1* | 5/2010 | Zevallos | ............... | E05B 1/0069 16/904 |
| 9,015,905 B1* | 4/2015 | Chen | ..................... | E05B 1/0069 16/904 |
| 2014/0137369 A1* | 5/2014 | Street | .................... | E05B 1/0069 16/111.1 |
| 2014/0208541 A1* | 7/2014 | Cowburn | .................. | B25G 1/00 16/110.1 |
| 2021/0197701 A1 | 7/2021 | Sakurai | | |

FOREIGN PATENT DOCUMENTS

| CN | 104816662 B | * | 3/2017 | ............... B60N 3/02 |
|---|---|---|---|---|
| CN | 111391739 A | * | 7/2020 | ............... B60N 3/02 |
| JP | 202045026 A | | 3/2020 | |
| JP | 202063049 A | | 4/2020 | |
| JP | 202063050 A | | 4/2020 | |
| JP | 2021104778 A | | 7/2021 | |
| KR | 20200008100 A | * | 1/2020 | |

* cited by examiner

*Primary Examiner* — Dennis H Pedder
(74) *Attorney, Agent, or Firm* — HAUPTMAN HAM, LLP (57) ABSTRACT

An entrance handrail includes an outer pipe that is supported by a supporting member provided in a proximity of an entrance of a vehicle, and that has a non-looped shape that is a shape obtained by removing a partial section from a looped-shape, an inner pipe supported inside of the outer pipe and exposed from the outer pipe at a partial section, the inner pipe having a looped-shape, a sheet member that is configured to be able to cover an outer peripheral face of the inner pipe, and that is movable in an axial direction of the inner pipe and the outer pipe by a drive device provided inside of the outer pipe, and a disinfecting device that is provided inside of the outer pipe and that is configured to disinfect the sheet member by irradiation of ultraviolet rays.

6 Claims, 12 Drawing Sheets

ENTRANCE HANDRAIL

CROSS-REFERENCE TO RELATED APPLICATION

This application claims priority to Japanese Patent Application No. 2020-143772 filed on Aug. 27, 2020, incorporated herein by reference in its entirety.

BACKGROUND

1. Technical Field

The disclosure relates to an entrance handrail.

2. Description of Related Art

There is conventionally known a hanging strap disinfecting device in which a light-shielding cover is provided above a handle of a hand strap, and a light-emitting element capable of emitting ultraviolet rays is provided on the interior of the cover, and the handle that is rotatable in the circumferential direction is disinfected as the upper portion of the handle that is covered by the cover is irradiated with the ultraviolet rays (see Japanese Unexamined Patent Application Publication No. 2020-063050 (JP 2020-063050 A), for example).

SUMMARY

Passengers reach from below to grasp hand straps, so the disinfecting device that has a cover such as described above at all times is practical. However, an entrance handrail that is installed in the proximity of an entrance of a bus or the like will be grasped by passengers from various directions. Accordingly, a disinfecting device that has such a cover at all times would make it difficult for passengers to grasp the entrance handrail, and the intended functions of the entrance handrail will be diminished.

The disclosure provides an entrance handrail that can be disinfected without diminishing functions of an entrance handrail.

An entrance handrail according to an aspect of the disclosure includes an outer pipe that is supported by a supporting member provided in a proximity of an entrance of a vehicle, and that has a non-looped shape that is a shape obtained by removing a partial section from a looped-shape, an inner pipe supported inside of the outer pipe and exposed from the outer pipe at a partial section, the inner pipe having a looped-shape, a sheet member that is configured to be able to cover an outer peripheral face of the inner pipe, and that is movable in an axial direction of the inner pipe and the outer pipe by a drive device provided inside of the outer pipe, and a disinfecting device that is provided inside of the outer pipe and that is configured to disinfect the sheet member by irradiation of ultraviolet rays.

According to the above aspect, when getting on and off of a vehicle, passengers grip the sheet member of the entrance handrail. Now, the sheet member is capable of being moved in the axial direction by the drive device, and can be disinfected by being irradiated with ultraviolet rays by the disinfecting device. Accordingly, when passengers are not gripping the sheet member of the entrance handrail, the sheet member can be moved in the axial direction and be disinfected. Thus, the entrance handrail can be disinfected without compromising the functions thereof.

In the above aspect, the drive device may be configured to move the sheet member in the axial direction by a predetermined amount each time the entrance is closed by a door.

According to the above configuration, each time the entrance is closed by the door, the sheet member is moved by a predetermined amount in the axial direction. That is to say, the sheet member is disinfected each time the entrance is closed by the door. Accordingly, the sheet member that passengers grip when getting on and off is constantly in a disinfected state, and the passengers can grip the sheet member assured.

In the above aspect, the drive device may be made up of rotating members, at least three to a set, that have sliding resistance as to the sheet member and that are disposed equidistantly in a circumferential direction of the outer pipe, with at least two sets being provided across a predetermined interval in the axial direction.

According to the above configuration, the drive device is made up of rotating members, at least three to a set, that have sliding resistance as to the sheet member and that are disposed equidistantly in the circumferential direction of the outer pipe, with at least two sets thereof provided across a predetermined interval in the axial direction. Accordingly, the sheet member can be smoothly moved in the axial direction.

In the above aspect, an outer diameter of a portion of the inner pipe that is disposed inside of the outer pipe may be smaller than an outer diameter of a portion of the inner pipe that is exposed from the outer pipe.

According to the above configuration, the outer diameter of a portion of the inner pipe that is disposed inside of the outer pipe is smaller than an outer diameter of a portion of the inner pipe that is exposed from the outer pipe. Accordingly, the sheet member can readily move in the axial direction through the inside of the outer pipe. Also, conversely, the outer diameter of the inner pipe is larger at the portion exposed from the outer pipe than at the portion disposed within the outer pipe, and accordingly, passengers can easily grip the sheet member covering the portion of the outer peripheral face of the inner pipe that is exposed from the outer pipe.

In the above aspect, the inner pipe may be supported inside of the outer pipe by a plurality of brackets disposed in one row on an inner peripheral face of the outer pipe following the axial direction. A portion of the sheet member that is exposed from the outer pipe may be made to have a cylindrical configuration, and a portion disposed inside of the outer pipe may be made to have a non-cylindrical configuration so as to be able to avoid the brackets, by a fastener mechanism.

According to the above configuration, the portion of the sheet member that is exposed from the outer pipe has a cylindrical configuration, and the portion disposed inside of the outer pipe has a non-cylindrical configuration so as to be able to avoid the brackets, by a fastener mechanism. Accordingly, the sheet member easily moves smoothly in the axial direction through inside of the outer pipe. Also, the passengers can grip only the disinfected sheet member, without touching the inner pipe.

In the above aspect, the supporting member may support the outer pipe such that the outer pipe is pivotable with a vehicle-up-down direction as an axial direction. The outer pipe may be configured to extend outward from the vehicle by pivoting centered on a rotation axis of the supporting member as a door operates to open the entrance, and to be stored within the vehicle by pivoting centered on the rotation axis of the supporting member as the door operates to close the entrance.

According to the above configuration, in accordance with the operation of the door to open the entrance, the outer pipe extends outward from the vehicle, and is stored in the vehicle in accordance with operation of the door to close the entrance. That is to say, when assuming the stored orientation, the entrance handrail does not extend toward the vehicle inward side (cabin side). This suppresses the entrance handrail from restricting riding space.

According to the above aspect, the entrance handrail can be disinfected without diminishing functions of an entrance handrail.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein.

DETAILED DESCRIPTION OF EMBODIMENTS

An embodiment of the disclosure will be described below in detail, with reference to the drawings. Note that an entrance handrail 30 according to the present embodiment is suitably provided to a small-sized bus (including Mobility as a Service (MaaS) vehicles of which automatically-driven busses are representative) 10, which is an example of an omnibus vehicle serving as a vehicle (see FIG. 1).

Accordingly, in the drawings, the arrow UP represents the vehicle upward direction of the bus 10, the arrow FR represents the vehicle forward direction of the bus 10, the arrow LH represents the vehicle left direction of the bus 10, for the sake of convenience, and the arrow RH represents the vehicle right direction of the bus 10, as appropriate. When the directions of up-down, front-rear, and right-left are made in the following description without any particular notation, these are to be understood to mean up-down in the vehicle up-down direction, front-rear in the vehicle front-rear direction, and right-left in the vehicle right-left direction (vehicle width direction).

Figure 1:
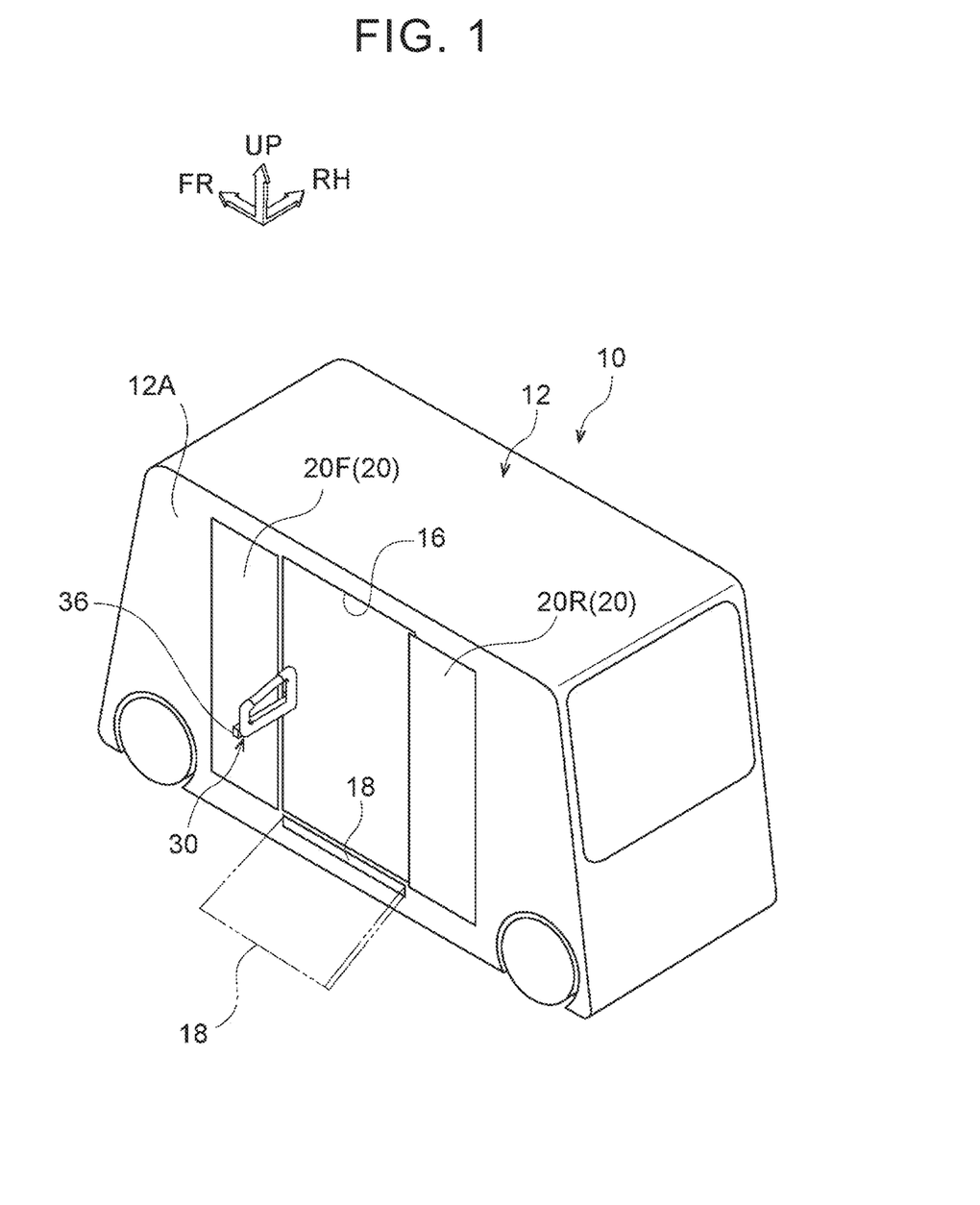
FIG. 1 is a perspective view illustrating a bus provided with an entrance handrail according to an embodiment.

An entrance 16 having a rectangular form in side view is provided at a generally middle portion in the front-rear direction of a left-side wall (one side wall) of a body 12 of the bus 10, as illustrated in FIG. 1. The bus 10 is provided with sliding doors 20 serving as a door that opens and closes the entrance 16.

The sliding doors 20 are made up of a front-side half-door 20F and a rear-side half-door 20R, each of which have a rectangular shape that is longer in the up-down direction than in the front-rear direction thereof in side view. The sliding doors 20 are configured to be able to open and close the entrance 16 as the front-side half-door 20F and the rear-side half-door 20R synchronously slide (move) along an outer wall face 12A of the bus 10, in directions away from each other and closer to each other.

An elastic member 22 (see FIG. 10) made of rubber or the like is attached to the front and rear direction inner side end faces of each of the half-doors 20F and 20R that come into contact with each other when the entrance 16 is closed (in other words, a rear end face of the half-door 20F and a front end face of the half-door 20R), over the entire length thereof in the up-down direction. That is to say, the half-doors 20F and 20R close the entrance 16 by coming into contact while elastically deforming the elastic members 22 of each other.

Figure 11:
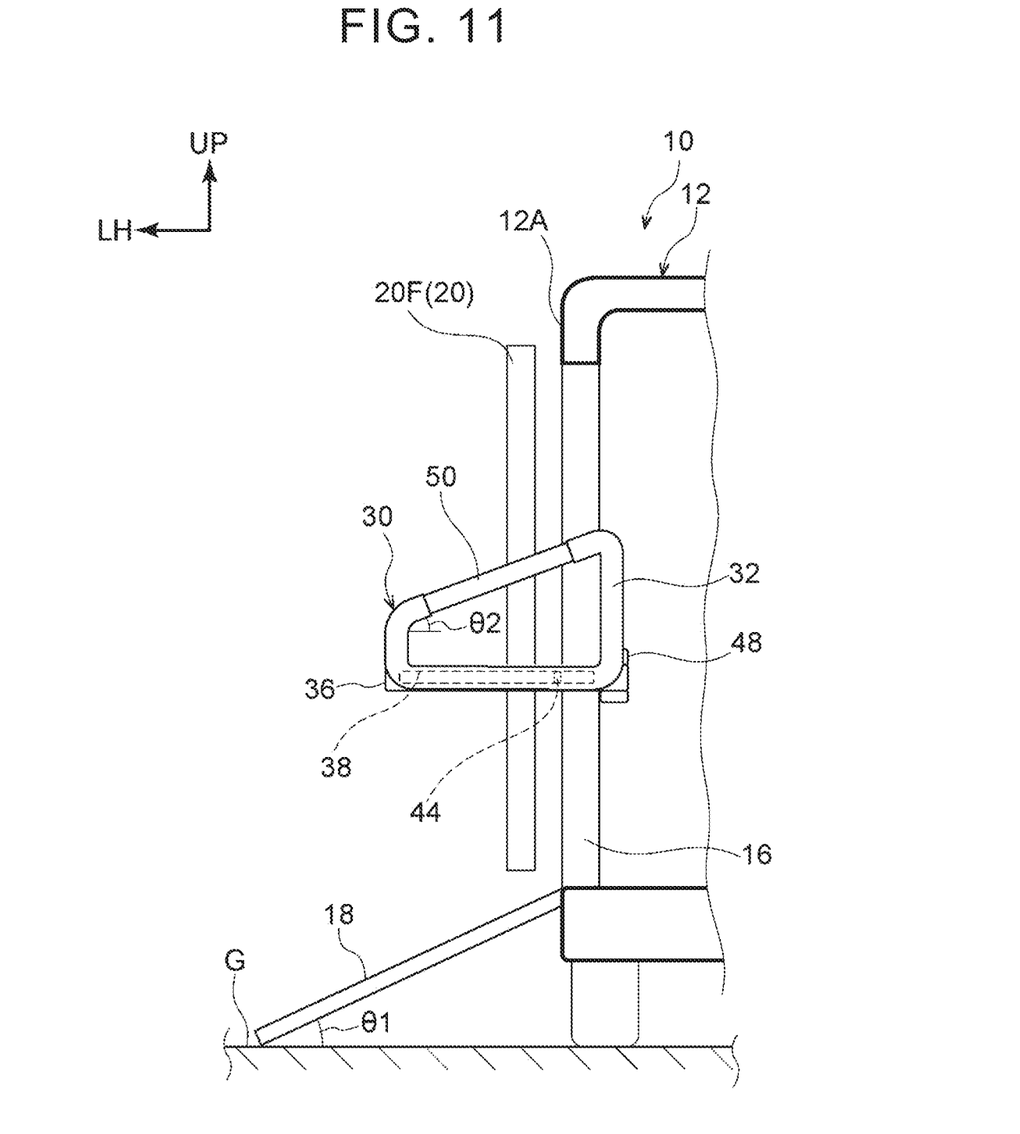
FIG. 11 is a rear face view illustrating a deployed orientation of the entrance handrail according to the embodiment.

Also, a slope 18 that is capable of extending outward from the vehicle is stored in the body 12 at the downward side of the entrance 16 (e.g., at the downward side of a floor panel), as illustrated in FIG. 1. The slope 18 is formed as a plate, and is configured to be drawn out and stored under electric power. A distal end portion of the slope 18 that is drawn out, in the direction of drawing out, is supported by a road surface G, thereby positioning the slope 18 at a predetermined inclination angle θ1, as illustrated in FIG. 11.

Also, as illustrated in FIG. 1, the entrance handrail 30, formed of metal (e.g., formed of aluminum) is arranged to extend outward in the vehicle width direction from a predetermined position in the up-down direction (height direction) of the entrance 16 when the sliding doors 20 (half-door 20F and half-door 20R) are slid (moved) and the entrance 16 is opened.

Figure 2:
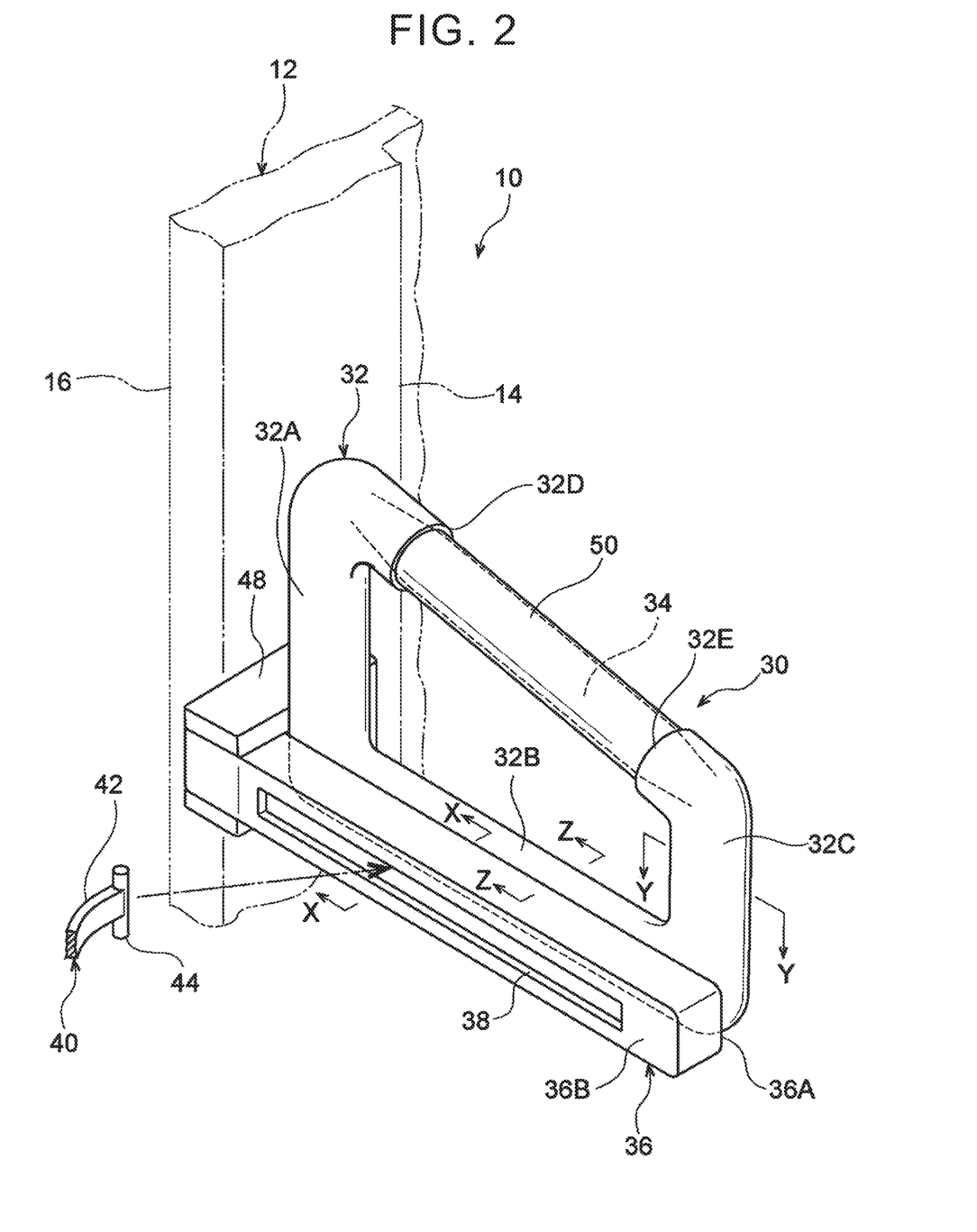
FIG. 2 is a perspective view illustrating the entrance handrail according to the embodiment.

To describe this in detail, the entrance handrail 30 includes a cylindrical outer pipe 32 having a non-looped shape that is a shape obtained by removing a partial section from a looped-shape (a general letter-C shape as viewed from a direction orthogonal to an axial direction), and an inner pipe 34 that has a looped-shape, is provided in a state that is being supported inside of the outer pipe 32 and exposed from the outer pipe 32 at the partial section, as illustrated in FIG. 2. That is to say, the length of the inner pipe 34 at the portion exposed from the outer pipe 32 is shorter than the length of the inner pipe 34 at the portion disposed inside the outer pipe 32. Note that the inner structure of the outer pipe 32 will be described later in detail. Here, the content "having a non-looped shape that is a shape obtained by removing a partial section from a looped-shape", is used for convenience sake in the explanation of the shape of the outer pipe 32. That is, the shape of the outer pipe 32 seems to be obtained by removing a partial section from a looped-shape, and the outer pipe 32 is not necessarily obtained by actually removing a partial section from a pipe member having a looped-shape.

The inner pipe 34 extends obliquely downward from the upper portion of the outer pipe 32, as illustrated in FIG. 2. That is to say, the inner pipe 34 is disposed inclined as to the horizontal direction, thereby forming a right-angled triangular shape with the outer pipe 32. An inclination angle θ2 of the inner pipe 34 as to the horizontal direction is an inclination angle that is approximately the same as the inclination angle θ1 of the slope 18, as illustrated in FIG. 11.

Figure 4:
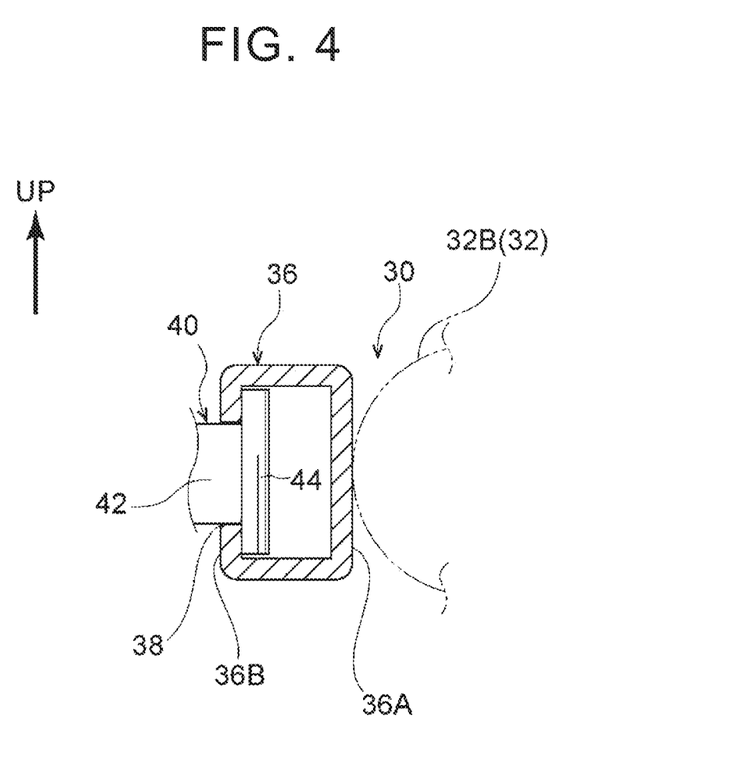
FIG. 4 is a cross-sectional view taken along line X-X in FIG. 2 as viewed from the direction of arrows, illustrating a state in which the sliding member is held by the rail member.
Figure 5:
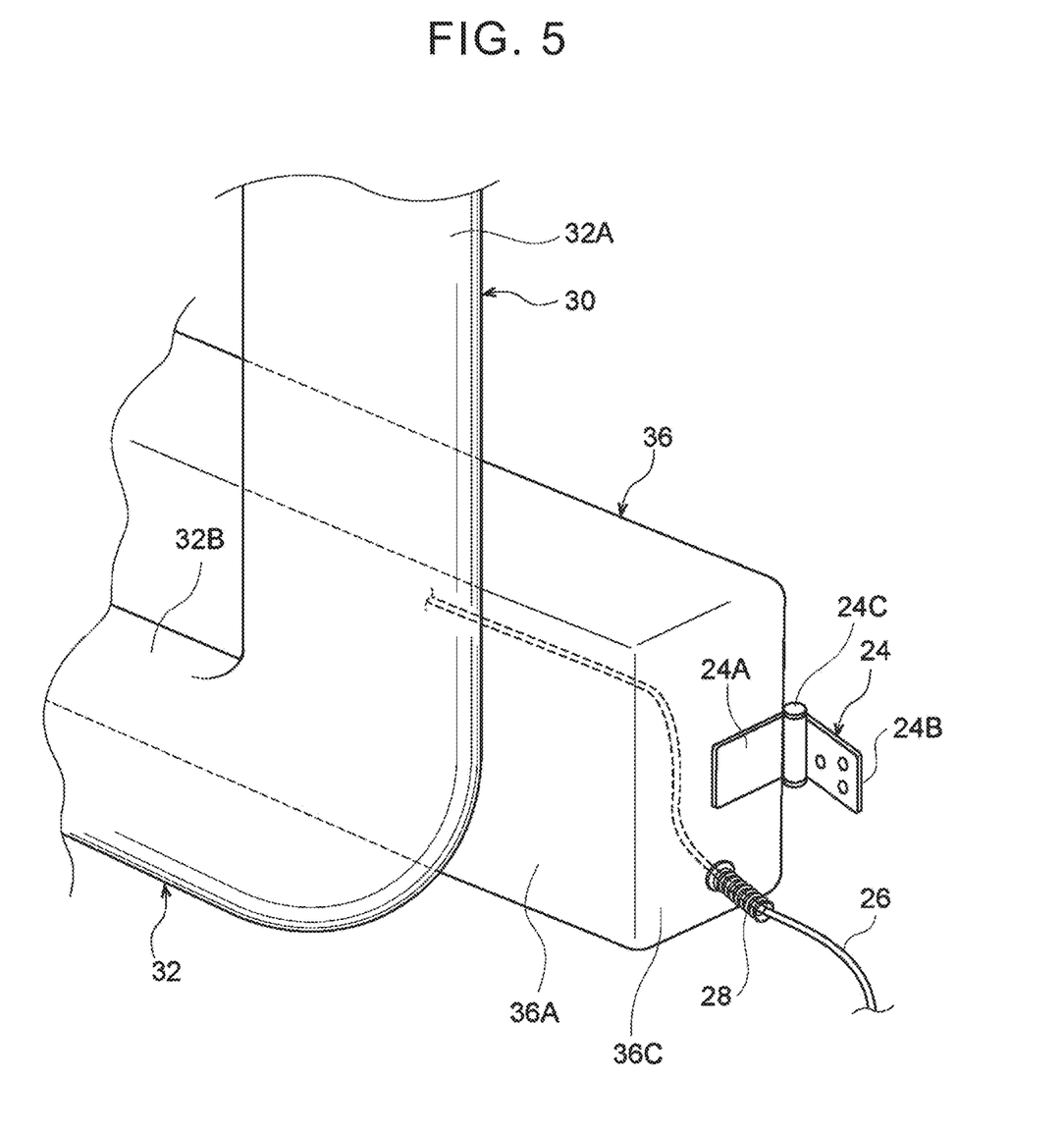
FIG. 5 is a perspective view illustrating a light-emitting element and a power feed cable to a drive device motor provided to the entrance handrail according to the embodiment.

Part of an outer peripheral face of the outer pipe 32 at a lower portion 32B thereof is fixed to a one side wall 36A of a rail member 36 serving as a supporting member provided in the proximity of the entrance 16 (e.g., an inner wall face of a pillar 14 illustrated in FIG. 2) of the bus 10, as illustrated in FIGS. 2, 4, and 5, by welding or the like.

The rail member 36 is configured as a square pipe (rectangular in cross-sectional form) in which the up-down direction serves as the long sides (see FIG. 4), with the horizontal direction extending as the longitudinal direction. A longitudinal-direction end portion of the rail member 36 is pivotably supported at an inner wall face of the pillar 14, with the up-down direction as the axial direction.

That is to say, one end portion 24A of a hinge 24 formed of metal is strongly attached to a longitudinal-direction one end face 36C of the rail member 36 by welding or the like, and another end portion 24B of the hinge 24 is strongly attached to an inner wall face of the pillar 14 by a plurality of bolts or the like. Thus, the entrance handrail 30 is capable of pivoting by 90 degrees or more in planar view, centered on a rotating shaft 24C of the hinge 24, through the rail member 36 also supported by a later-described sliding member 40.

Also, an insertion opening (omitted from illustration) for a power feed cable 26 is provided in the longitudinal-direction one end face 36C of the rail member 36. The cable 26 is laid out passing from a battery (omitted from illustration) installed in the bus 10, through the interior of the pillar 14. The cable 26 is then inserted from a supply opening (omitted from illustration) provided on an inner wall face of the pillar 14 into an insertion opening of the rail member 36, and further from a supply opening (omitted from illustration) of the rail member 36 into an insertion opening (omitted from illustration) of the outer pipe 32. That is to say, the cable 26 is laid out to the inside of the outer pipe 32.

Note that the insertion opening of the rail member 36 is covered by a rubber accordion boot 28 fit over the cable 26. Also, the hinge 24, part of the cable 26 exposed between the supply opening of the pillar 14 and the insertion opening of the rail member 36, and the boot 28, are covered by a rectangular box-shaped cover member 48 (see FIG. 2) attached to the pillar 14.

The rail member 36 is arranged to slidably support the sliding member 40 (see FIG. 3) attached to an inner-side end portion in the front-rear direction of the half-door 20F, for example, of the sliding door 20, as illustrated in FIG. 2. To describe this in detail, a slit portion 38 is provided in another side wall 36B of the rail member 36 (a side wall facing the forward side when in a later-described deployed orientation, and facing the outer side in the vehicle width direction when in a later-described stored orientation), in the general middle portion in the up-down direction thereof. The slit portion 38 communicates with the inside of the rail member 36 and is provided to have a predetermined length following the extending direction (longitudinal direction) thereof.

Figure 3:
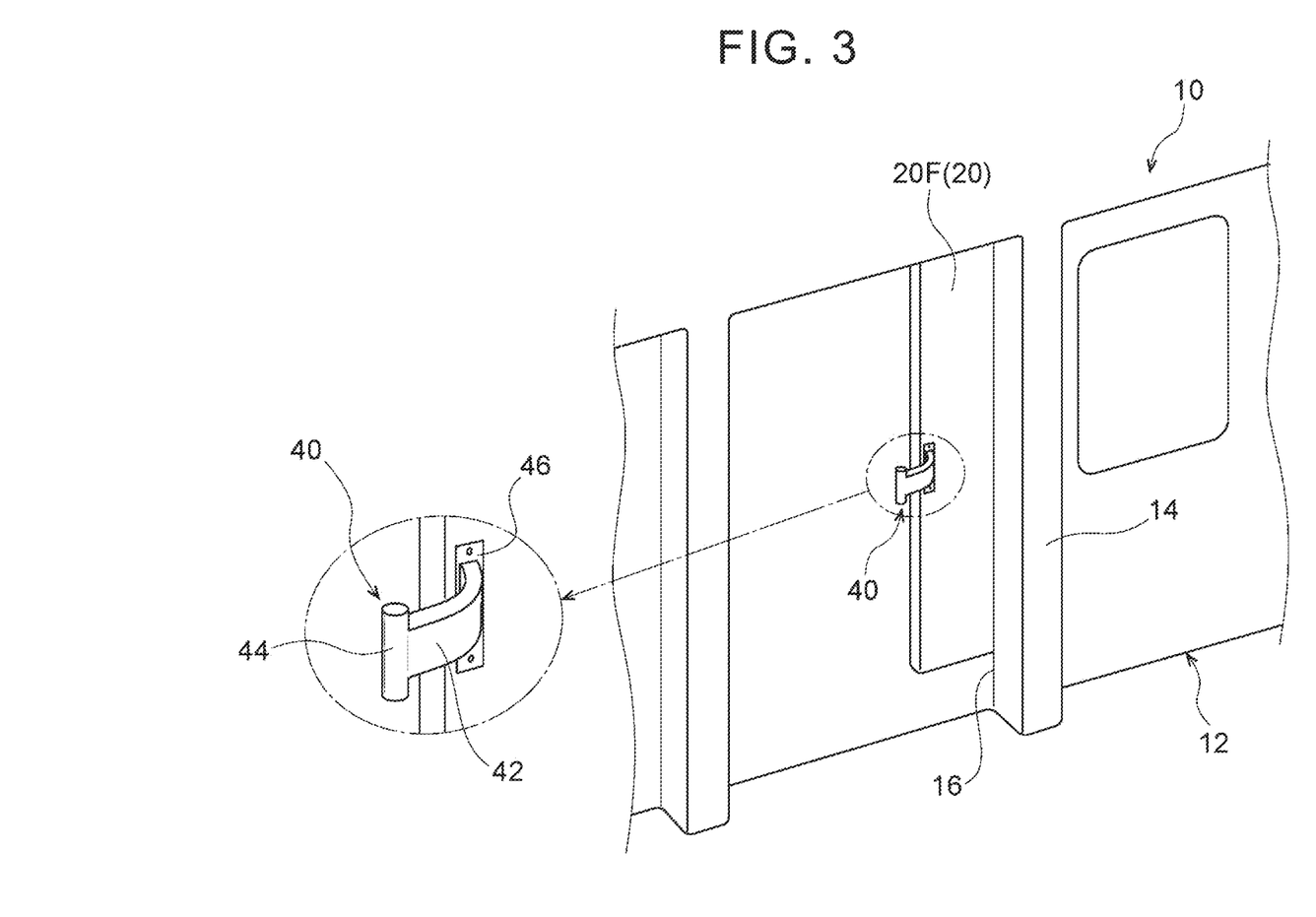
FIG. 3 is a perspective view illustrating a sliding member that a rail member of the entrance handrail according to the embodiment slidably holds.

On the other hand, the sliding member 40 has a general letter-T shape in side view, as illustrated in FIG. 3. That is to say, the sliding member 40 has a main unit portion 42 that is in a curved-plate form in planar view, a generally post-shaped fitting portion 44 protruding in the up and down directions (with the up-down direction as the axial direction) from the distal end of the main unit portion 42, and a plate-shaped fixing portion 46 provided on a base end on the opposite side of the main unit portion 42 from the fitting portion 44.

The sliding member 40 is attached to the rail member 36 before the fixing portion 46 is attached to the half-door 20F. Specifically, the fitting portion 44 of the sliding member 40 is passed through the slit portion 38 of the rail member 36 sideways (with the axial direction horizontally oriented), and then is rotated by 90 degrees. Accordingly, the fitting portion 44 of the sliding member 40 is fit to the rail member 36 so as to be slidable in the longitudinal direction thereof without coming loose from the rail member 36, as illustrated in FIG. 4.

Accordingly, the width of the slit portion 38 (the gap in the up-down direction) is configured to be larger than the outer diameter of the fitting portion 44, and the same as the width of the main unit portion 42 of the sliding member 40 (the length following the axial direction of the fitting portion 44 in side view) or slightly larger. After fitting the fitting portion 44 to the rail member 36, the fixing portion 46 of the sliding member 40 is attached to the inner-side end portion in the front-rear direction of the half-door 20F by bolting or the like. The rail member 36 is thus configured to be supported by the sliding member 40 as well.

The outer diameter of the inner pipe 34 is smaller at the portion thereof disposed within the outer pipe 32 as compared to the portion exposed from the outer pipe 32 (at the partial section), as illustrated in FIG. 2 and FIGS. 6 through 8. Note that the outer diameter of the inner pipe 34 at the portion exposed from the outer pipe 32 is the same as a size obtained by subtracting at least the thickness of a later-described sheet member 50 from the inner diameter of the outer pipe 32.

Also, the outer diameter of the inner pipe 34 disposed inside an opening-side one-end portion 32D and an opening-side other-end portion 32E of the outer pipe 32 is gradually reduced. The inner pipe 34 of which the diameter is smaller is supported at the inside of the outer pipe 32 by a plurality of brackets 33 arrayed in one row following the axial direction along the inner peripheral face of the outer pipe 32 (e.g., one within a base portion 32A, two within the lower portion 32B, and one within a distal end portion 32C).

Figure 6:
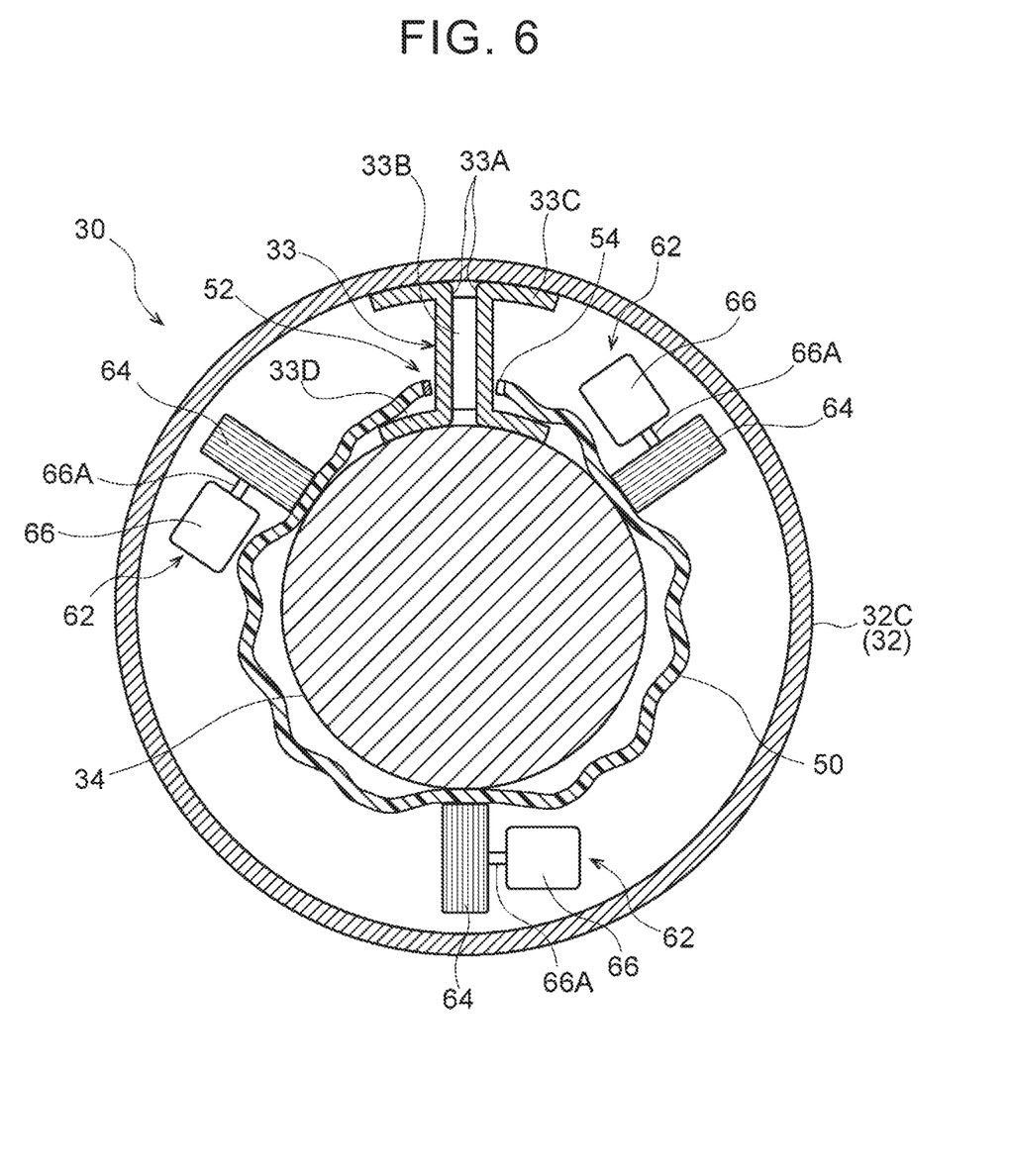
FIG. 6 is a cross-sectional view taken along line Y-Y in FIG. 2 as viewed from the direction of arrows, illustrating an internal structure of a distal end portion side of the entrance handrail according to the embodiment.
Figure 7:
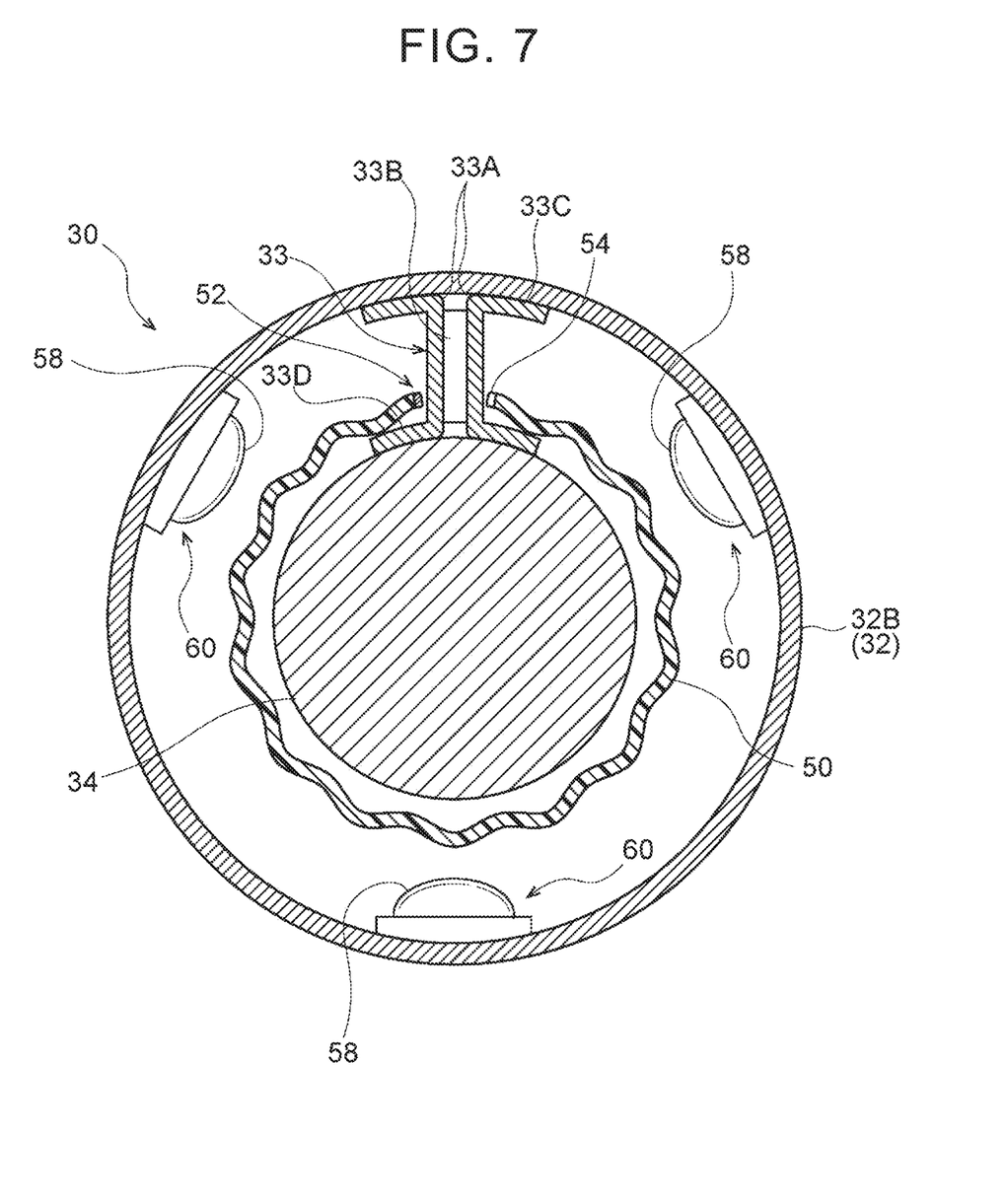
FIG. 7 is a cross-sectional view taken along line Z-Z in FIG. 2 as viewed from the direction of arrows, illustrating an internal structure of a lower portion side of the entrance handrail according to the embodiment.

The brackets 33 each have a configuration in which a pair of main unit portions 33A, each having a general letter-U shape in a cross-sectional view taken along a plane perpendicular to the axial direction, is integrally joined by a plate-like linking portion 33B, with the open portion sides of the general letter-U shapes facing away from each other, as illustrated in FIGS. 6 and 7. One flange portion 33C of each bracket 33 in the radial direction of the inner pipe 34 (outer pipe 32) is fixed to a part of the inner peripheral face of the outer pipe 32 by welding or the like, and another flange portion 33D of each bracket 33 is fixed to a portion of the outer peripheral face of the inner pipe 34 by welding or the like.

Accordingly, the one (outer side in the radial direction) flange portion 33C of each bracket 33 has an arc shape following the inner peripheral face of the outer pipe 32, and the other (inner side in the radial direction) flange portion 33D of each bracket 33 has an arc shape following the outer peripheral face of the inner pipe 34. According to this configuration, the inner pipe 34 is concentrically disposed inside the outer pipe 32 by the brackets 33.

The sheet member 50 configured to be capable of covering the outer peripheral face of the entire inner pipe 34 is provided on the inner peripheral face side of the outer pipe 32 and on the outer peripheral face side of the inner pipe 34. The sheet member 50 is the portion that passengers grasp, and is formed of a material that has relatively low stretchability, such as a fiber material having water repellency and antibacterial properties, a rubber material used for medical gloves, or the like.

The sheet member 50 is movable in the axial direction of the inner pipe 34 and the outer pipe 32 by a drive device 62 provided inside the outer pipe 32. To describe this in detail, the drive device 62 is made up of rollers formed of rubber (hereinafter referred to as "rubber rollers") 64 serving as rotating members having sliding resistance (friction) as to the sheet member 50 supported on the outer peripheral face of the inner pipe 34 (nipping the sheet member 50 between the outer peripheral face of the inner pipe 34 and the rubber rollers 64, and feeding the sheet member 50), three to a set, and drive motors 66 that rotate each of the rubber rollers 64 in one direction.

Each drive motor 66 is supported on the inner peripheral face of the outer pipe 32 by a bracket (omitted from illustration). Each rotating shaft 66A of each drive motor 66 is fixed concentrically with the axial portion of each rubber roller 64. Thus, the rubber rollers 64 are configured to rotate synchronously in one direction by the rotational driving force of the drive motors 66. Note that the set of three rubber rollers 64 is positioned equidistantly in the circumferential direction of the outer pipe 32. It is sufficient for at least three of the rubber rollers 64 to be provided in the circumferential direction, and four or more may be provided. The rubber rollers 64 preferably have no texturing on the outer peripheral faces thereof.

It is sufficient for at least two sets of the drive devices 62 made up of the rubber rollers 64 and drive motors 66, three to a set, to be provided with a predetermined interval therebetween in the axial direction of the outer pipe 32. That is to say, it is sufficient for the drive devices 62 to be provided at least in the base portion 32A and the distal end portion 32C of the outer pipe 32, for example. FIG. 6 illustrates the drive device 62 provided within the distal end portion 32C.

Figure 8:
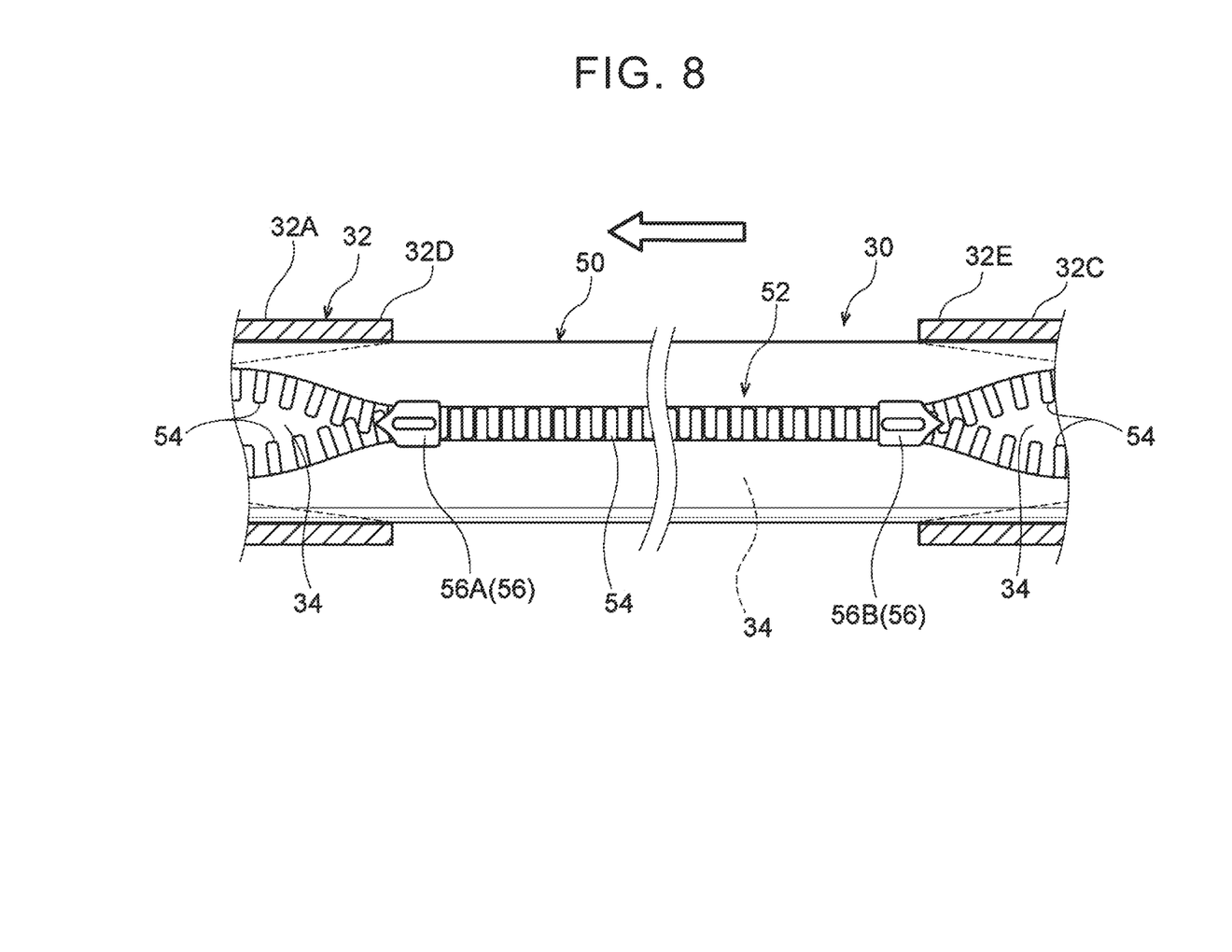
FIG. 8 is a bottom view illustrating a sheet member side of the entrance handrail according to the embodiment.

The sheet member 50 has a cylindrical configuration at the portion exposed from the outer pipe 32, due to a fastener mechanism 52 provided on the lower face thereof, following the axial direction, and has a non-cylindrical configuration so as to be able to avoid the brackets (omitted from illustration) at portions disposed inside the outer pipe 32, as illustrated in FIG. 8.

That is to say, elements 54 are provided following the axial direction on the lower face of the sheet member 50, and a pair of sliders 56 is provided to the elements 54, provided facing in opposite directions from each other (with the sides interlocking the elements 54 opposed). Each slider 56 is fixed on the inner peripheral faces of the opening-side one-end portion 32D and the opening-side other-end portion 32E of the outer pipe 32 via brackets (omitted from illustration).

Accordingly, the sheet member 50 is configured such that, when the sheet member 50 moves in the axial direction indicated by an arrow in FIG. 8, the interlocking of elements 54 with each other is disengaged by a slider 56A on the downstream side in the direction of movement, and the sheet member 50 can move in the axial direction while avoiding the brackets 33 (See FIGS. 6 and 7).

The sheet member 50 is also configured such that, when moving in the axial direction, the elements 54 are interlocked with each other by a slider 56B on the upstream side in the direction of movement, and thus the sheet member 50 covers the entire circumference of the outer peripheral face of the portion of the inner pipe 34 that is exposed from the outer pipe 32 (partial section).

Also, a disinfecting device 60 that disinfects the sheet member 50 by irradiating the outer peripheral face of the sheet member 50 moving in the axial direction with ultraviolet rays is provided inside the lower portion 32B of the outer pipe 32, as illustrated in FIG. 7. The disinfecting device 60 is made up of a plurality of (e.g., three) ultraviolet ray emitting elements (hereinafter referred to simply as "light-emitting elements") 58 attached to the inner peripheral face of the outer pipe 32.

The light-emitting elements 58 are laid out in a staggered pattern on the inner peripheral face of the lower portion 32B of the outer pipe 32, for example, at predetermined intervals in the axial direction. That is to say, the light-emitting elements 58 are provided at mutually different positions on the lower portion 32B of the outer pipe 32 in the axial direction and in the circumferential direction, at equidistant positions when viewed from the axial direction and the circumferential direction.

Accordingly, a configuration is made in which the outer peripheral face of the sheet member 50 moving through the inside of the outer pipe 32 in the axial direction can be thoroughly irradiated with ultraviolet rays. Note that electric power is fed to the drive motors 66 and the light-emitting elements 58 by the cable 26 laid out to the inside of the outer pipe 32.

Also, turning the light-emitting element 58 on and off, and rotating and stopping of the drive motors 66, are controlled by a control device (omitted from illustration) provided to the bus 10. To describe this in detail, when the control device recognizes that the entrance 16 is closed by the sliding doors 20, the control device outputs a signal to feed power to the light-emitting elements 58 and turn the light-emitting elements 58 on, and also outputs a signal to feed power to the drive motors 66 and move the sheet member 50 by a predetermined amount in the axial direction of the inner pipe 34 and the outer pipe 32.

The term "predetermined amount" as used here means the amount to move at least part of the sheet member 50 that was exposed from the outer pipe 32 before moving in the axial direction, to a position of being accommodated within the outer pipe 32. In other words, this refers to an amount of moving part of the sheet member 50 that has been irradiated with ultraviolet rays and disinfected inside of the outer pipe 32, to a position where the outer peripheral face of the inner pipe 34 at the portion exposed from the outer pipe 32 (partial section) is completely covered.

The movement of the predetermined amount (including stopping after moving) is performed by the control device controlling the number of rotations of each drive motor 66, taking into consideration the amount of the sheet member 50 moved in the axial direction by each rubber roller 64 of the set of three in the drive device 62 rotating once. The control device is configured to output a signal to stop power feed to the light-emitting elements 58 and turn the light-emitting elements 58 off when the control device recognizes that the entrance 16 will be opened by the sliding doors next.

The configuration is such that the above (driving of the drive motors 66 and turning the light-emitting elements 58 on, in order to move the sheet member 50 by a predetermined amount in the axial direction of the inner pipe 34 and the outer pipe 32), is repeated each time the entrance 16 is closed by the sliding doors 20, thereby constantly keeping part of the sheet member 50 gripped by passengers at the time of getting on or off sterilized (disinfected) by ultraviolet rays. Note that the timing of turning the light-emitting elements 58 off is not limited to when the entrance 16 will be opened by the sliding doors 20 next, and may be after a predetermined amount of time has elapsed with the entrance 16 closed by the sliding doors 20.

The operations of the entrance handrail 30 according to the present embodiment, having the above-describe configuration, will be described next.

Figure 9:
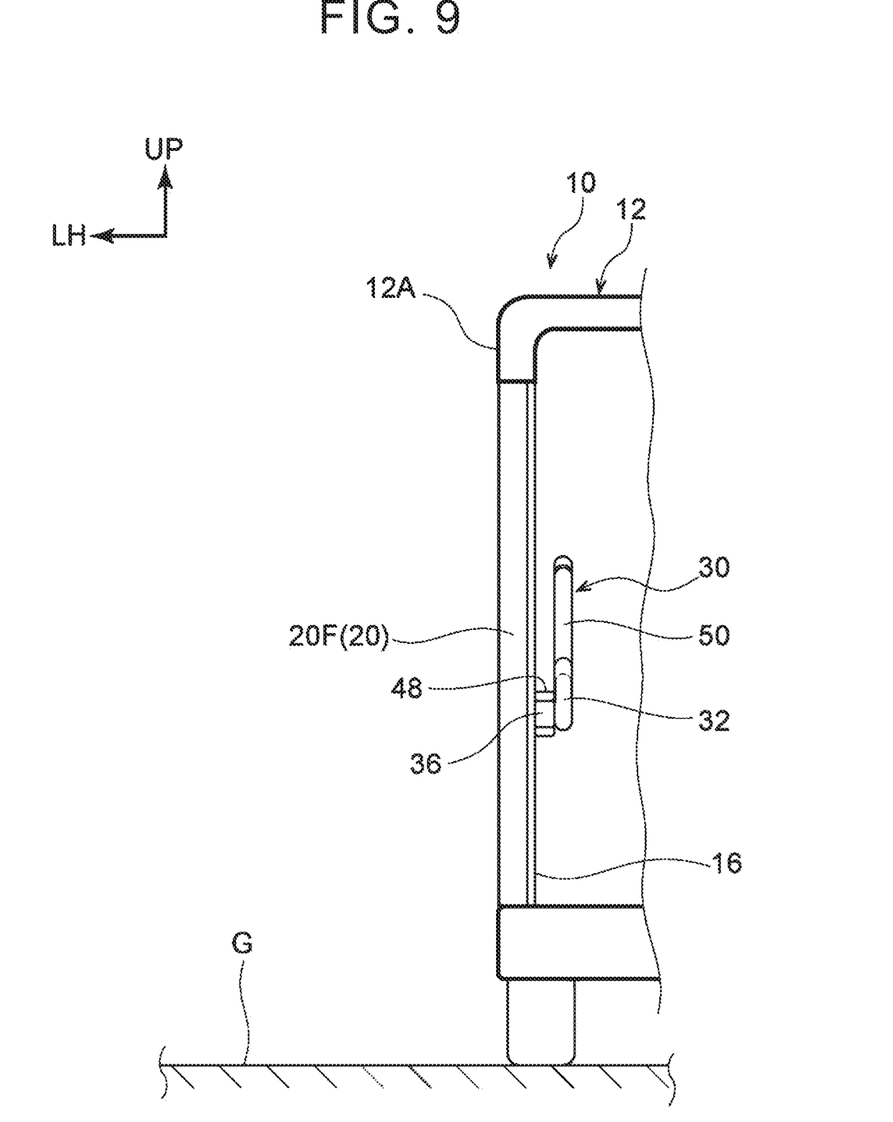
FIG. 9 is a rear face view illustrating a storage orientation of the entrance handrail according to the embodiment.
Figure 10:
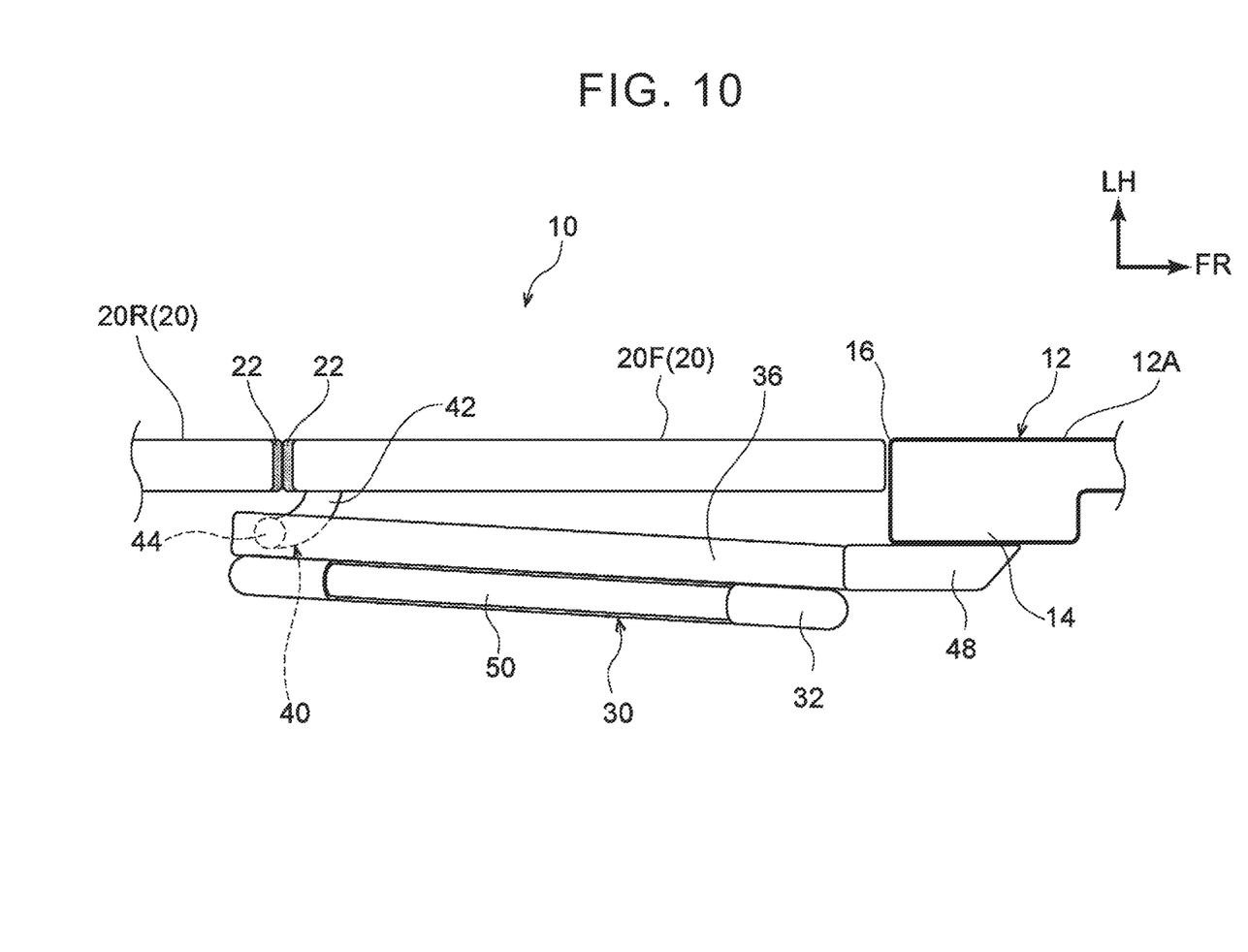
FIG. 10 is a planar view illustrating the storage orientation of the entrance handrail according to the embodiment.

When the entrance 16 is closed by the sliding doors 20 (half-doors 20F and 20R), the entrance handrail 30 is disposed approximately following the sliding doors 20 (the half-door 20F in the case illustrated here), as illustrated in planar view in FIGS. 9 and 10. Specifically, in a state in which the entrance 16 is closed by the sliding doors 20, the sliding member 40 has slidden to the distal end portion 32C following the rail member 36, assuming a stored orientation in which the sheet member 50 (inner pipe 34) and the rail member 36 are disposed following the sliding door 20.

That is to say, when assuming the stored orientation, the sheet member 50 (inner pipe 34) and the rail member 36 of the entrance handrail 30 do not extend toward the vehicle inward side (cabin side). Accordingly, in a small-sized bus 10 in particular, the provided entrance handrail 30 can be kept from restricting riding space thereof (riding space can be maximally secured).

Figure 12:
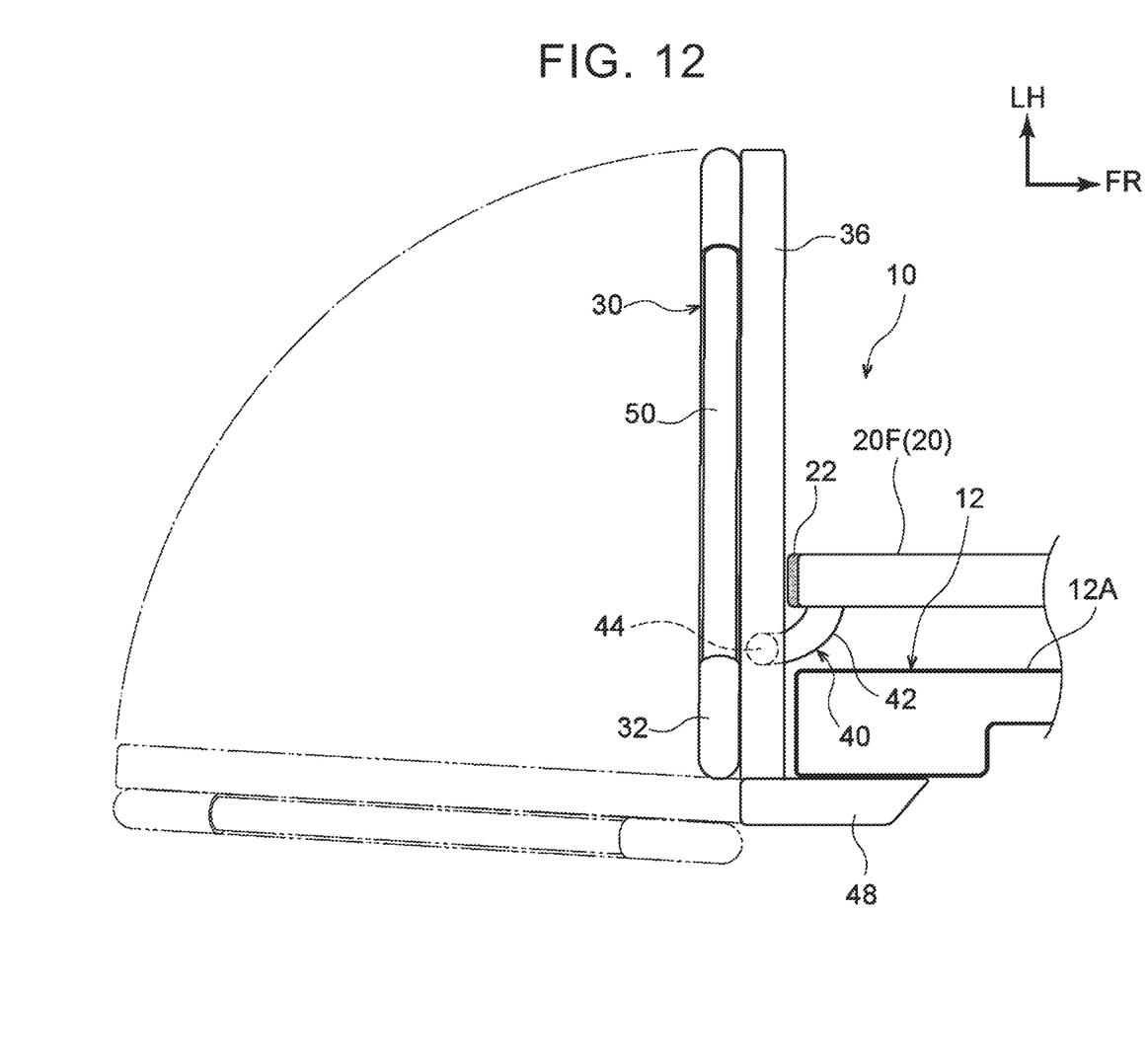
FIG. 12 is a planar view illustrating the deployed orientation of the entrance handrail according to the embodiment.

On the other hand, when the entrance 16 is opened by the sliding doors 20 (half-doors 20F and 20R), the entrance handrail 30 extends outward from the vehicle in planar view, as illustrated in FIGS. 11 and 12. Specifically, in a state in which the entrance 16 is opened by the sliding doors 20, the sliding member 40 has slidden to the base portion 32A side following the rail member 36, and a deployed orientation is assumed in which the sheet member 50 (inner pipe 34) and the rail member 36 extend outward from the vehicle (outer side in vehicle width direction).

Accordingly, passengers can grip the sheet member 50 (inner pipe 34) when getting on and off the bus 10, and accordingly getting on and off of the bus 10 is made easier (passengers can get on and off while stabilizing their posture). Particularly, when getting off, at the instant of lowering one foot downward, the passengers stand on the other foot. Providing the sheet member 50 (inner pipe 34) in the direction of movement facilitates firmly gripping, and the posture can be stabilized better.

Also, the sheet member 50 (inner pipe 34) extends obliquely toward the downward side from above the base portion 32A. Accordingly, when a bus 10 has the slope 18 provided at the bottom of the entrance 16, for example, the inclination angle θ1 of the slope 18 and the inclination angle θ2 of the sheet member 50 (inner pipe 34) can be made to approximately match (can be made to be generally parallel in rear view). Accordingly, when passengers use the slope 18 to get on or off, the height of the position of grasping can be made to change in accordance with how far the body is from the ground, and accordingly getting on and off while grasping the sheet member 50 (inner pipe 34) is made easier (passengers can get on and off while stabilizing their posture even better).

Note that when the entrance handrail 30 is in the deployed orientation, a sufficiently large gap is provided between the elastic member 22 attached to the inner side end face in the front-rear direction of the half-door 20F and the sheet member 50 (inner pipe 34) for a finger to be insertable. Accordingly, even if a finger is inserted between the elastic member 22 and the sheet member 50 (inner pipe 34) when getting on or off while gripping the sheet member 50 (inner pipe 34) (even if a finger comes into contact with the elastic member 22), there is no concern of that finger being hurt. That is to say, safety of the passengers is secured.

Also, when the control device recognizes that the entrance 16 is closed by the sliding doors 20, the drive motors 66 are rotationally driven, the sheet member 50 moves in the axial direction of the inner pipe 34 and the outer pipe 32 by the predetermined amount, and the light-emitting elements 58 are turned on, under control of the control device.

Now, the light-emitting elements 58 are disposed in a staggered pattern on the inner peripheral face on the lower portion 32B of the outer pipe 32 at predetermined intervals in the axial direction (provided at mutually different positions in the axial direction and the circumferential direction, and at equidistant positions when viewed from the axial direction and the circumferential direction). Accordingly, when the light-emitting elements 58 are turned on while moving the sheet member 50 in the axial direction, the sheet member 50 accommodated in the lower portion 32B of the outer pipe 32 is thoroughly irradiated with ultraviolet rays in the axial direction and circumferential direction.

Accordingly, the outer peripheral face of the sheet member 50 gripped by passengers before the entrance 16 being closed by the sliding doors 20 is sequentially sent in the axial direction (within the lower portion 32B) and is sterilized (disinfected) when passengers are not gripping the sheet member 50. Moreover, such sterilization of the sheet member 50 is executed each time the entrance 16 is closed by the sliding doors 20. Accordingly, passengers getting on or off the bus 10 next can grip the sheet member 50 (inner pipe 34) in a state of constantly being disinfected and kept sanitary (in a state replaced with a sanitary face).

Particularly, passengers riding the bus 10 can tell that the sheet member 50 is moving in the axial direction, and accordingly can recognize that the sheet member 50 is being sterilized (disinfected). Hence, the passengers riding the bus 10 can be assured regarding gripping the sheet member 50 (inner pipe 34), and can grip the sheet member 50 (inner pipe 34) without hesitation (assured). Thus, safety at the time of getting on and off of the bus 10 can be further improved.

Also, the drive device 62 is made up of sets of three rubber rollers 64 having sliding resistance (friction) as to the sheet member 50 supported on the outer peripheral face of the inner pipe 34 (nipping the sheet member 50 between the outer peripheral face of the inner pipe 34 and the rubber rollers 64, and feeding the sheet member 50). At least two drive devices 62 provided with the sets of three rubber rollers 64 are provided with a predetermined interval therebetween in the axial direction of the outer pipe 32. Accordingly, the sheet member 50 is smoothly moved in the axial direction of the inner pipe 34 and the outer pipe 32.

Also, the outer diameter of the inner pipe 34 is smaller at the portions disposed inside the outer pipe 32 than the portion exposed from the outer pipe 32 (partial section). Accordingly, the sheet member 50 can readily move in the axial direction through the inside of outer pipe 32, as compared to when the outer diameter of the inner pipe 34 is the same as the outer diameter of the portion exposed from the outer pipe 32 over the entire axial direction of the outer pipe 32.

Also, conversely, the outer diameter of the inner pipe 34 is larger at the portion exposed from the outer pipe 32

(partial section) than the portion disposed within the outer pipe 32. That is to say, the rigidity of the portion of the inner pipe 34 exposed from the outer pipe 32 is greater than the rigidity of the portion of the inner pipe 34 disposed inside the outer pipe 32. Accordingly, passengers can easily grip the sheet member 50 covering the outer peripheral face of the inner pipe 34 at the portion exposed from the outer pipe 32 (facilitates firm gripping).

Further, the fastener mechanism 52 causes the sheet member 50 to have a cylindrical configuration at the portion exposed from the outer pipe 32, and to have a non-cylindrical configuration at portions disposed inside the outer pipe 32, so as to be able to avoid the brackets 33. Accordingly, it is easy for the sheet member 50 to smoothly move in the axial direction inside the outer pipe 32. The passengers can also grip just the disinfected sheet member 50 without touching the outer peripheral face of the inner pipe 34.

Also, the disinfecting device 60 is provided inside of the outer pipe 32. Accordingly, the sheet member 50 (inner pipe 34) can be gripped from various directions as compared with when the disinfecting device 60 is provided outside of the outer pipe 32. Thus, the functions of the entrance handrail 30 are not compromised even in a configuration in which the disinfecting device 60 capable of irradiating the sheet member 50 with ultraviolet rays is provided.

After the light-emitting elements 58 are turned on, when the control device recognizes that the entrance 16 is going to be opened by the sliding doors 20 next, the light-emitting elements 58 are turned on under control by the control device. Accordingly, consumption of battery charge can be suppressed as compared to a configuration in which a state in which the light-emitting elements 58 are on is maintained even while the entrance 16 is opened by the sliding doors 20.

Also, the entrance handrail 30 is not limited to a configuration of being provided to just one half-door (e.g., the half-door 20F) side of the sliding doors 20. The entrance handrail 30 may have a configuration of being provided to both the one half-door (e.g., the half-door 20F) side and the other half-door (e.g., half-door 20R) side of the sliding doors 20.

Note however, that in this case, the entrance handrail 30 provided to the half-door 20R side is disposed offset in the up-down direction as to the entrance handrail 30 provided to the half-door 20F side. The reason is that due to the structure of the entrance handrails 30, the other end portion of the rail member 36 (distal end portion 32C of the outer pipe 32) provided to the half-door 20F side extends to the half-door 20R side, and the other end portion of the rail member 36 (distal end portion 32C of the outer pipe 32) provided to the half-door 20R side extends to the half-door 20F side.

This provides an advantage in that passengers of various heights can select and grip the sheet member 50 (inner pipe 34) that matches their own height, due to the entrance handrail 30 provided to the half-door 20R side being offset in the up-down direction as to the entrance handrail 30 provided to the half-door 20F side. As a matter of course, the positions of the sliding members 40 attached to each of the half-doors 20F and 20R are disposed offset in the up-down direction as well, in accordance with the positions of the entrance handrails 30.

Although the entrance handrail 30 according to the present embodiment has been described above with reference to the drawings, the entrance handrail 30 according to the present embodiment is not limited to that illustrated, and various design changes may be made as appropriate without departing from the essence of the disclosure. For example, the supporting member that pivotably supports the entrance handrail 30 is not limited to the rail member 36 that is illustrated, and any configuration (shape) may be employed, as long as it is capable of slidably holding the sliding member 40 without interfering with the layout of the cable 26.

Also, the rotating members that move the sheet member 50 in the axial direction of the inner pipe 34 and outer pipe 32 is not limited to the rubber rollers 64. The rotating members may be made up of rotating gears (omitted from illustration) or the like, for example, as long as they have sliding resistance (friction) as to the sheet member 50 supported on the outer peripheral face of the inner pipe 34. Also, the disinfecting device 60 is not limited to being made up of the light-emitting elements 58, and may be any configuration as long as it is configured to be capable of irradiation of ultraviolet rays.

Also, driving the drive motors 66 and turning the light-emitting elements 58 on is not limited to a configuration of being triggered by the control device recognizing closing of the sliding doors 20, and may be configured such that a switching operation performed by a driver of the bus 10, for example, to close the sliding door 20, serves as a trigger. Note however, that a configuration, in which the control device recognizing closing of the sliding doors 20 is a trigger, enables application to automatically-driven busses with no driver on board.

What is claimed is:

1. An entrance handrail, comprising:
   an outer pipe that is supported by a supporting member provided in a proximity of an entrance of a vehicle, and that has a non-looped shape that is a shape obtained by removing a partial section from a looped-shape;
   an inner pipe supported inside of the outer pipe and exposed from the outer pipe at a partial section;
   a sheet member that is able to cover an outer peripheral face of the inner pipe, and that is movable in an axial direction of the inner pipe and the outer pipe by a drive device provided inside of the outer pipe; and
   a disinfecting device that is provided inside of the outer pipe and that is configured to disinfect the sheet member by irradiation of ultraviolet rays.

2. The entrance handrail according to claim 1, wherein the drive device is configured to move the sheet member in the axial direction by a predetermined amount each time the entrance is closed by a door.

3. The entrance handrail according to claim 1, wherein the drive device is made up of rotating members, at least three to a set, that have sliding resistance as to the sheet member and that are disposed equidistantly in a circumferential direction of the outer pipe, with at least two sets being provided across a predetermined interval in the axial direction.

4. The entrance handrail according to claim 1, wherein an outer diameter of a portion of the inner pipe that is disposed inside of the outer pipe is smaller than an outer diameter of a portion of the inner pipe that is exposed from the outer pipe.

5. The entrance handrail according to claim 1, wherein:
   the inner pipe is supported inside of the outer pipe by a plurality of brackets disposed in one row on an inner peripheral face of the outer pipe following the axial direction; and
   a portion of the sheet member that is exposed from the outer pipe is made to have a cylindrical configuration, and a portion disposed inside of the outer pipe is made to have a non-cylindrical configuration so as to be able to avoid the brackets, by a fastener mechanism.

6. The entrance handrail according to claim 1, wherein:
the supporting member supports the outer pipe such that the outer pipe is pivotable with a vehicle-up-down direction as an axial direction; and
the outer pipe is configured to extend outward from the vehicle by pivoting centered on a rotation axis of the supporting member as a door operates to open the entrance, and to be stored within the vehicle by pivoting centered on the rotation axis of the supporting member as the door operates to close the entrance.

* * * * *